United States Patent [19]

Brady et al.

[11] Patent Number: 5,653,753
[45] Date of Patent: Aug. 5, 1997

[54] METHOD AND APPARATUS FOR FOLDING OF INTRAOCULAR LENSES

[75] Inventors: Daniel G. Brady, San Juan Capistrano, Calif.; Bernard F. Grisoni, Cordova, Tenn.

[73] Assignee: Allergan, Waco, Tex.

[21] Appl. No.: 487,762

[22] Filed: Jun. 7, 1995

Related U.S. Application Data

[62] Division of Ser. No. 235,444, Apr. 29, 1994.
[51] Int. Cl.$^6$ ...................................................... A61F 2/16
[52] U.S. Cl. .................................... 623/6; 606/107
[58] Field of Search ........................ 623/6; 606/107; 81/3.44

[56] References Cited

U.S. PATENT DOCUMENTS

| | | | |
|---|---|---|---|
| 278,192 | 5/1883 | Stanwood | 81/3.44 |
| 450,266 | 4/1891 | Truax . | |
| 1,641,152 | 9/1927 | Burleigh | 81/3.44 |
| 1,994,415 | 3/1935 | Edwards | 81/3.44 |
| 2,001,346 | 5/1935 | Hays | 81/3.44 |
| 2,450,138 | 10/1948 | Harwood . | |
| 2,505,859 | 5/1950 | Jockisch | 81/3.44 |
| 3,678,927 | 7/1972 | Soichet . | |
| 3,703,174 | 11/1972 | Smith . | |
| 4,026,281 | 5/1977 | Mayberry et al. . | |
| 4,122,556 | 10/1978 | Poler . | |
| 4,179,954 | 12/1979 | Whalen | 81/3.44 |
| 4,190,049 | 2/1980 | Hager et al. . | |
| 4,198,980 | 4/1980 | Clark . | |
| 4,214,585 | 7/1980 | Bailey, Jr. . | |
| 4,244,370 | 1/1981 | Furlow et al. . | |
| 4,249,271 | 2/1981 | Poler . | |
| 4,251,887 | 2/1981 | Anis . | |
| 4,253,199 | 3/1981 | Banko . | |
| 4,257,521 | 3/1981 | Poler . | |
| 4,298,994 | 11/1981 | Clayman . | |
| 4,303,268 | 12/1981 | Davidson . | |
| 4,325,375 | 4/1982 | Nevyas . | |
| 4,349,027 | 9/1982 | DiFrancesio . | |
| 4,373,218 | 2/1983 | Schachar . | |
| 4,423,809 | 1/1984 | Mazzocco . | |
| 4,446,581 | 5/1984 | Blake . | |
| 4,449,257 | 5/1984 | Koeniger . | |
| 4,462,404 | 7/1984 | Schwarz et al. . | |
| 4,463,457 | 8/1984 | Kelman . | |
| 4,468,820 | 9/1984 | Uhler et al. . | |
| 4,490,860 | 1/1985 | Rainin . | |
| 4,527,294 | 7/1985 | Heslin | 623/6 |
| 4,573,998 | 3/1986 | Mazzucco | 623/6 |
| 4,597,379 | 7/1986 | Kihn | 606/33 |

(List continued on next page.)

FOREIGN PATENT DOCUMENTS

| | | |
|---|---|---|
| 0270257 | 8/1988 | European Pat. Off. . |
| 0340698 | 8/1989 | European Pat. Off. . |
| 2191439 | 12/1987 | United Kingdom . |
| 8201646 | 5/1982 | WIPO . |
| 8808288 | 11/1988 | WIPO . |
| 9420027 | 9/1994 | WIPO . |

OTHER PUBLICATIONS

STAAR Surgical Co., vol. 4, No. 1, 1988.
Cataract Refract Surg., vol. 15, Mar. 1989, Christ et al pp. 176–184.
Folding & Inserting Silicone Intraocular Lens Implants, Faulkner, Nov. 1987.
Microsert II™, Model IM002, Directions for Use with the Chiroflex™II, Chiron IntraOptics, Jul., 1993.

*Primary Examiner*—Randy C. Shay
*Attorney, Agent, or Firm*—Frank J. Uxa

[57] ABSTRACT

A method of inserting a foldable intraocular lens (IOL) into the eye of a patient comprising holding a foldable IOL with forceps with the IOL being in a first folded condition in which the IOL has at least one fold and folding the IOL into a second folded condition in which the IOL has at least the first fold and a second fold. The IOL is retained in the second folded condition in a tubular member. The IOL is then transferred in substantially the second folded condition into the eye of the patient.

6 Claims, 4 Drawing Sheets

U.S. PATENT DOCUMENTS

| | | | |
|---|---|---|---|
| 4,600,004 | 7/1986 | Lopez et al. | 623/6 |
| 4,619,657 | 10/1986 | Keates et al. | 623/6 |
| 4,681,102 | 7/1987 | Bartell | 623/6 |
| 4,702,244 | 10/1987 | Mazzocco | 623/6 |
| 4,715,373 | 12/1987 | Mazzocco et al. | 623/6 |
| 4,732,150 | 3/1988 | Keener, Jr. | |
| 4,747,404 | 5/1988 | Jampel et al. | 623/6 |
| 4,759,359 | 7/1988 | Willis et al. | 623/6 |
| 4,763,650 | 8/1988 | Hauser | 623/6 |
| 4,765,329 | 8/1988 | Cumming et al. | 623/6 |
| 4,769,034 | 9/1988 | Poley | 623/6 |
| 4,781,719 | 11/1988 | Kelman | 623/6 |
| 4,785,810 | 11/1988 | Baccala et al. | 623/6 |
| 4,791,924 | 12/1988 | Kelman | |
| 4,813,957 | 3/1989 | McDonald | 623/6 |
| 4,819,631 | 4/1989 | Poley | 623/6 |
| 4,834,094 | 5/1989 | Patton et al. | 623/6 |
| 4,836,201 | 6/1989 | Patton et al. | 623/6 |
| 4,844,065 | 7/1989 | Faulkner | |
| 4,844,093 | 7/1989 | Jampel et al. | |
| 4,880,000 | 11/1989 | Holmes et al. | 623/6 |
| 4,917,680 | 4/1990 | Poley | 623/6 |
| 4,919,130 | 4/1990 | Stoy et al. | 606/107 |
| 4,934,363 | 6/1990 | Smith et al. | 606/107 |
| 4,976,716 | 12/1990 | Cumming | 606/107 |
| 4,988,352 | 1/1991 | Poley | 623/6 |
| 5,098,439 | 3/1992 | Hill et al. | 606/107 |
| 5,123,905 | 6/1992 | Kelman | 606/107 |
| 5,176,686 | 1/1993 | Poley | 623/6 |
| 5,190,552 | 3/1993 | Kelman | 606/107 |
| 5,260,021 | 11/1993 | Zeleznick | |
| 5,275,604 | 1/1994 | Rheinish et al. | 623/6 |
| 5,549,614 | 8/1996 | Tunis | 623/6 |

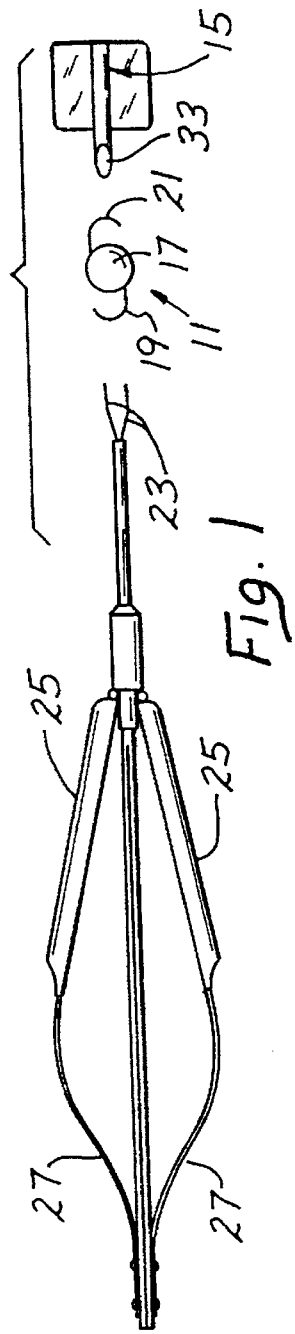
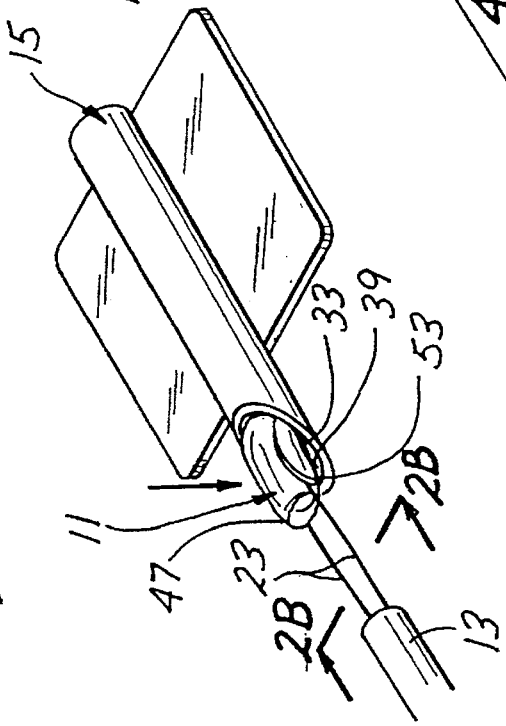
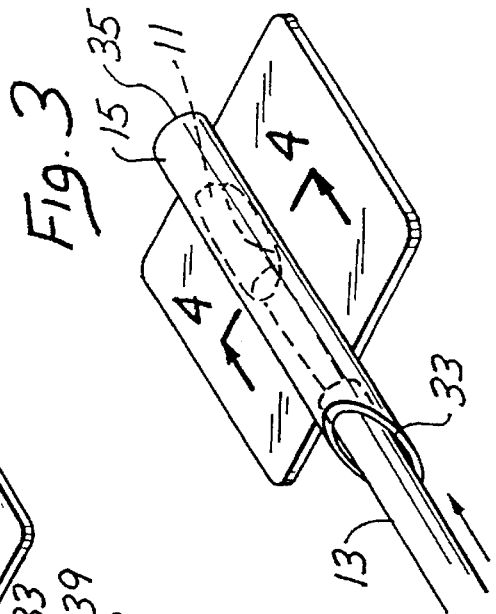
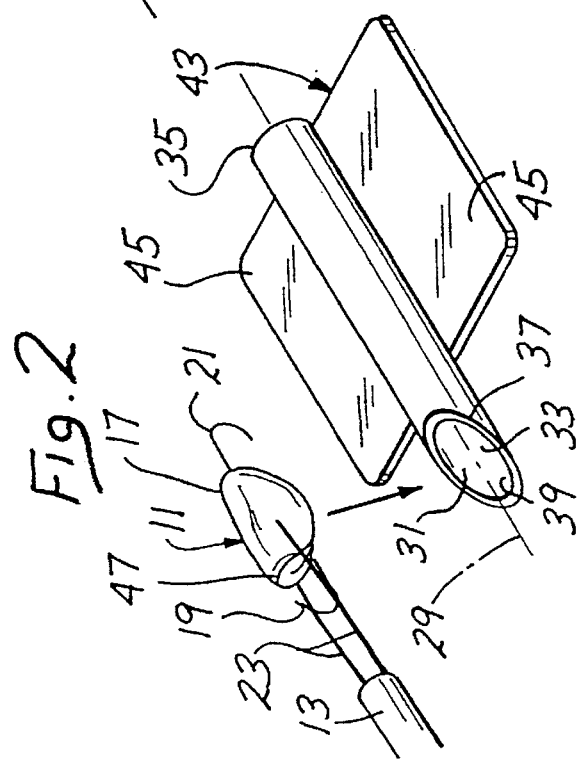

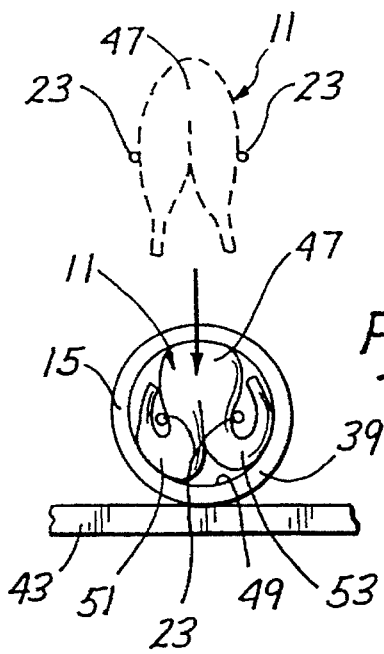
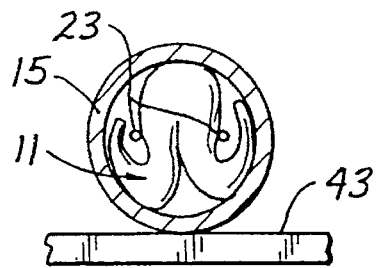
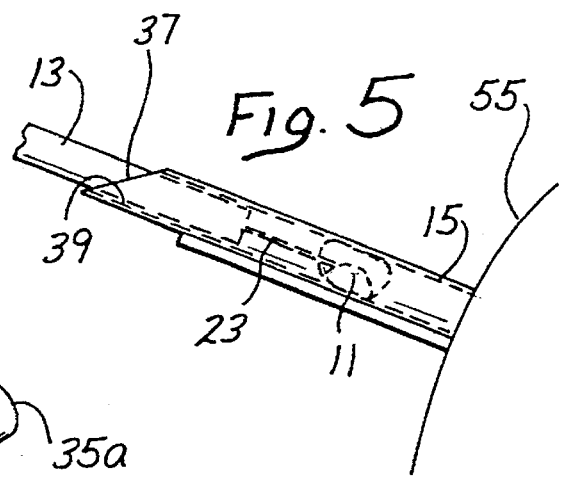
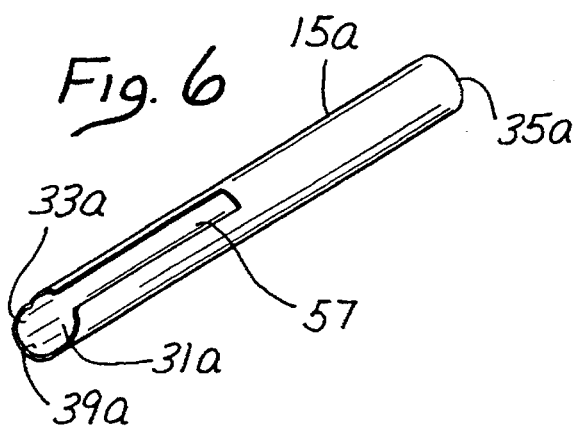
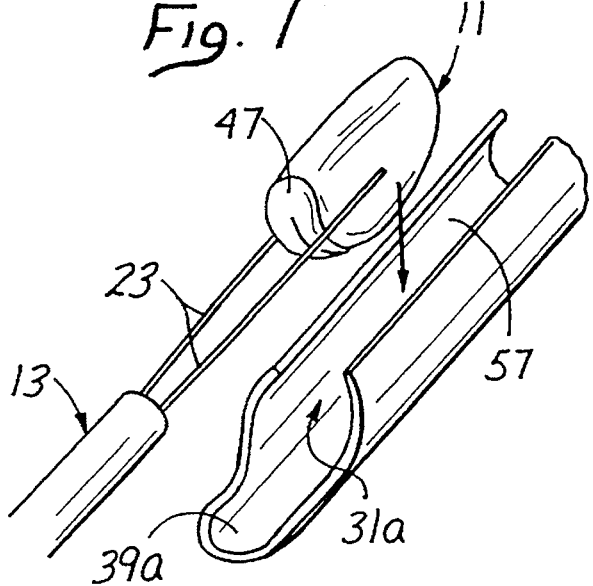
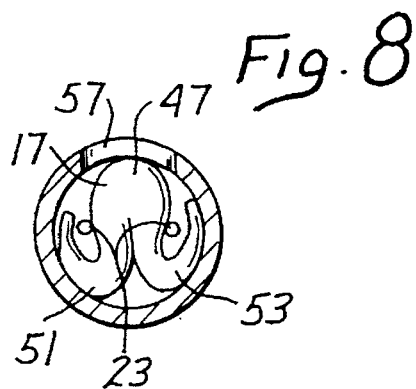

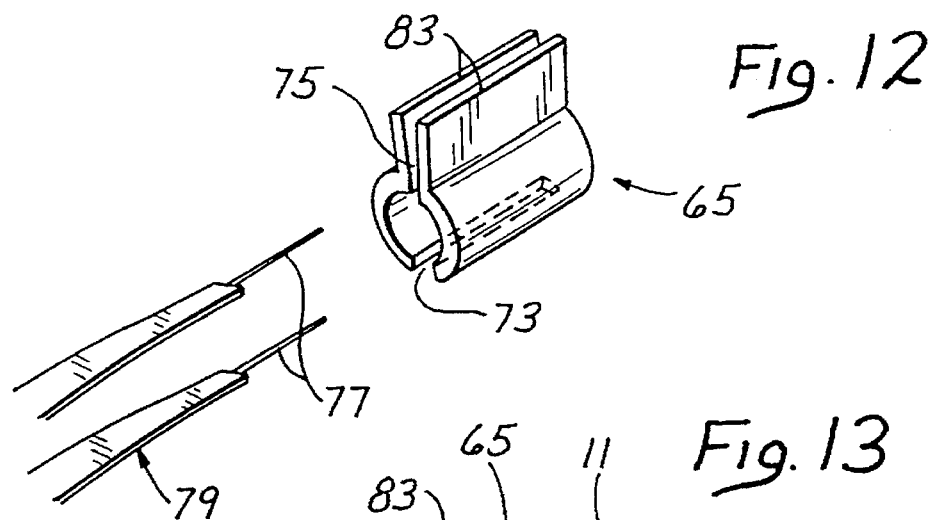
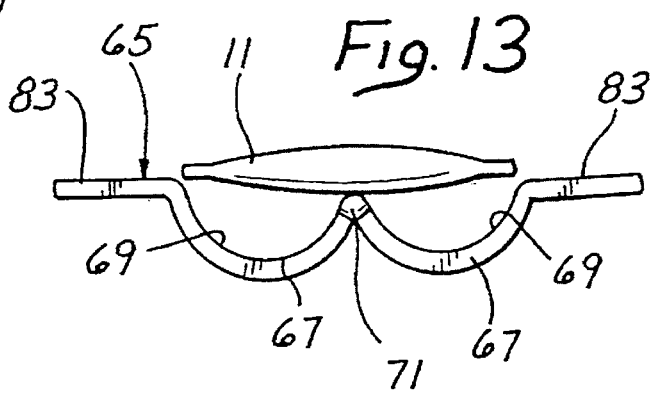
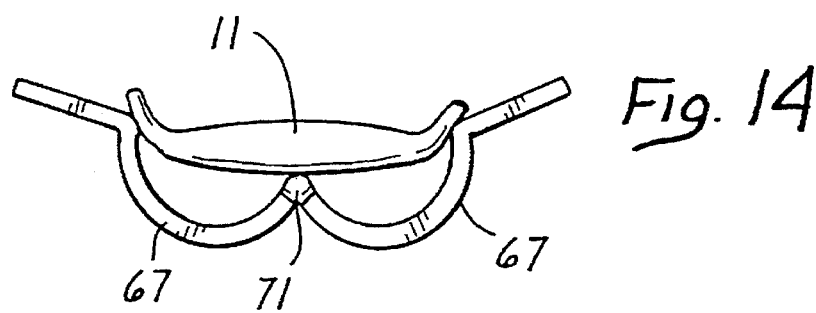
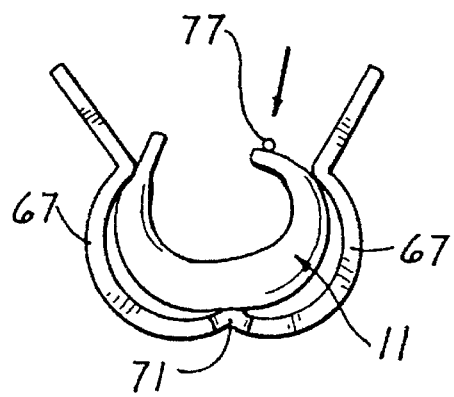
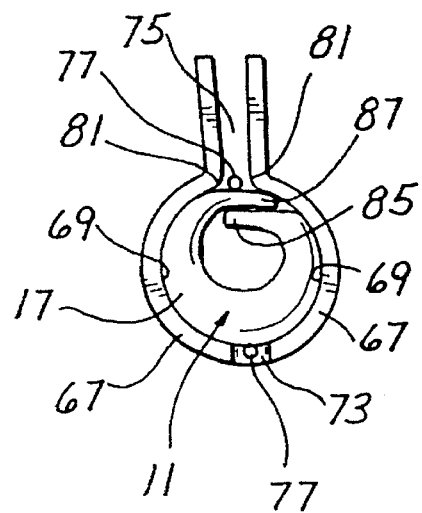

METHOD AND APPARATUS FOR FOLDING OF INTRAOCULAR LENSES

This application is a division of application Ser. No. 08/235,444, filed Apr. 29, 1994.

FIELD OF THE INVENTION

This invention relates to a method and apparatus for inserting a foldable intraocular lens (IOL) into the eye of a patient and to a method and apparatus for folding the IOL.

BACKGROUND OF THE INVENTION

As is well known, an IOL is used to replace the natural lens of the human eye when the natural lens becomes incapable of functioning as desired. A typical IOL includes an optic or lens and one or more fixation members for fixing the IOL in the desired position within the eye.

The optic of an IOL may be constructed of hard, nondeformable materials such as polymethylmethacrylate or of soft, deformable materials such as silicone based or acrylic based materials. One advantage of the deformable IOL's is that they can be deformed into a configuration which permits them to be inserted through a smaller incision into the eye.

In deforming the IOL, the optic is typically folded in a way to cause the IOL to have smaller dimensions which enables it to be inserted through a smaller incision. An IOL which is deformed by forming it into a roll is also folded in the sense that the roll constitutes at least one fold. As used herein, a folded optic, folded IOL and folded condition have reference to an optic which is deformed in any manner, including rolling, that produces a fold.

It is desirable to compactly fold a foldable IOL because this can minimize the length of the incision necessary to insert the folded IOL into the eye. However, because IOL's are very small, they are difficult to grasp and even more difficult to fold into an efficient, compact configuration of minimal dimensions. As an example of size, the optic of a foldable IOL may be in the neighborhood of about 5 to about 7 millimeters in diameter.

Various devices have been proposed for use in folding a foldable IOL. For example, a forceps can be used to provide a single fold in an IOL which, in effect, folds the IOL in half. This, however, is not a configuration which in general will minimize the length of the incision needed for insertion of the IOL into the eye. Mazzocco U.S. Pat. No. 4,573,998 discloses forceps of a particular configuration for use in conjunction with other devices which apparently provide multiple folds in an IOL. However, this patent does not disclose how the folds are initially formed in the IOL.

SUMMARY OF THE INVENTION

This invention provides a method for inserting a foldable IOL into the eye of a patient which generally overcomes the disadvantages identified above. With this invention, the IOL can be efficiently, compactly and relatively easily folded into a folded condition that includes at least first and second folds. Also, the folded IOL can be relatively easily transferred to the eye of the patient.

According to one feature of the invention, a foldable IOL is held in a first folded condition in which the IOL has at least one fold. The IOL is folded into a second folded condition in which the IOL has at least the first fold and a second fold. The multiple folds provide a compact configuration of reduced dimensions. The IOL is retained in the second folded condition in a tubular member. The IOL is then transferred substantially in the second folded condition from the tubular member to the eye of the patient.

With this technique placing the IOL in the first folded condition, which may include only a single fold, can be relatively easily carried out using conventional techniques, such as a forceps. The second folded condition can advantageously be obtained by urging or pressing the IOL against a surface. The second folded condition includes at least one additional fold and preferably at least a third fold. The configuration currently preferred, although not necessary to carry out this invention, is a second folded condition in which the IOL is generally in the form of a W. The first and second folds also preferably face in generally opposite directions.

The tubular member provides a number of important advantages. For example, the surface against which the IOL is urged to fold it into the second folded condition can advantageously be provided by the tubular member. For example, the tubular member may include a platform adjacent one end of the tubular member which provides the surface against which the IOL can be urged. With this construction, the IOL can then be easily moved, as by sliding, into the tubular member for retention in the second folded condition.

To facilitate insertion of the IOL into the tubular member, the tubular member has a bore and preferably has an opening with a radially extending component leading to the bore. This enables the opening to be accessed from the side. With this arrangement, the IOL can be inserted through the opening into the bore while it is grasped by the forceps with the IOL forming, for example, one or two additional folds around the arms of the forceps.

By providing the opening with the radially extending component at one end of the tubular member, the tubular member provides, in effect, the platform against which the foldable IOL can be pressed by the forceps. Of course, the platform may be in various different configurations. Alternatively, the opening with a radially extending component may be a radial opening in the peripheral wall of the tubular member. In this event the forceps may be used to insert the IOL through the opening in the peripheral wall of the tubular member. The surface against which the IOL is urged to fold the IOL into the second folded condition may be the surface which defines the bore. Urging of the IOL against this surface will at least assist in folding the IOL into the second folded condition.

In addition to holding the IOL in the second folded condition, the tubular member also facilitates transferring the IOL to the eye of the patient. This can be accomplished in various different ways as, for example, by pushing the IOL through the tubular member and the incision into the eye. This step of pushing may be carried with the forceps or another member, such as a plunger. Alternatively, the IOL in the second folded condition may be withdrawn from the tubular member with an insertion tool, such as forceps, and inserted through the incision into the eye. To facilitate the withdrawal of the IOL from the tubular member, the tubular member may have generally opposed first and second slots opening at one end of the tubular member with these slots being sized and arranged such that the arms of the forceps can be received through the slots, respectively, to grip the IOL.

An important feature oft he invention, whether or not the IOL is held with forceps, is the folding of the IOL from a first folded condition into a second folded condition in which the IOL has at least one more fold than in the first folded condition. Insertion through either an open end of the tubular member or through an opening in the peripheral wall of the tubular member retains the IOL in the second folded condition. If desired, the IOL in the second folded condition may be packaged and stored within the tubular member in which event, it is retained within the tubular member for a substantial period of time. However, at present it is preferred to retain the folded IOL in the tubular member only briefly as part of an implantation procedure. For example, the IOL may be pushed through the tubular member continuously or intermittently and in the former case, the IOL is retained by the tubular member in the second folded condition only while it is moving through the tubular member.

According to another feature of the invention, the IOL is provided in any suitable manner in a folded condition in a tubular member and the IOL is removed from the tubular member in substantially the folded condition using forceps. Using forceps, the IOL is then transferred in substantially the folded condition through an incision into the eye of the patient.

Another feature of the invention is to provide a folder for folding an IOL. The folder includes first and second jaws and a hinge such that the jaws can be pivoted between a loading position in which the jaws can receive an IOL and a folded position in which concave surfaces of the jaws are in generally confronting relationship. The jaws are adapted to fold the IOL as they move from the loading position to the folded position. The jaws have opposite ends and define generally opposed slots opening at one of the ends for receiving the arms of forceps. One of the slots may be defined, for example, by spacing apart free ends of the jaws.

In one form, the tubular member has a peripheral wall with an opening leading to a bore with the opening being sized and adapted to allow passage of a folded IOL through the opening and into the bore. The tubular member has first and second generally opposed slots opening at an open end of the tubular member, and these slots are sized to receive first and second arms, respectively, of forceps.

In another form, the tubular member has opposite end faces with an opening at each of the end faces leading to the bore in the tubular member. One of the end faces is inclined at an acute angle relative to the central axis of the bore and a flange is coupled to the tubular member and extends laterally outwardly of the tubular member.

The invention, together with additional features and advantages thereof may best be understood by reference to the following description taken in connection with the accompanying illustrative drawings.

BRIEF DESCRIPTION OF THE DRAWINGS

FIG. 1 is a plan view illustrating forceps, a preferred tubular member and a foldable IOL.

FIG. 2 is a perspective view illustrating the forceps holding the IOL in a first folded condition near an opening of the tubular member.

FIG. 2A is a perspective view illustrating the folding of the IOL into the second folded condition.

FIG. 2B is a sectional view taken generally along line 2B—2B of FIG. 2A. The IOL is illustrated in the first folded condition in dashed lines.

FIG. 3 is a perspective view similar to FIG. 2 illustrating the IOL in the second folded condition inserted by the forceps into the tubular member.

FIG. 4 is an enlarged sectional view taken generally along lines 4—4 of FIG. 3.

FIG. 5 is a side elevational view illustrating one technique for transferring IOL substantially in the second folded condition from the tubular member to the eye of the patient.

FIG. 6 is a perspective view of a second form of tubular member.

FIG. 7 is a perspective view showing the IOL held with forceps in a first folded condition and about to be inserted through an opening in a peripheral wall of the tubular member.

FIG. 8 is a sectional view similar to FIG. 4 illustrating the IOL in the second folded condition within the tubular member of FIG. 6.

FIG. 12 is a perspective view of forceps and one form of folder.

FIG. 13 is an end elevational view of the folder of FIG. 12 in the loading position and of an IOL in the folder.

FIGS. 14 and 15 are end elevational views of the folder being pivoted toward the folded position shown in FIG. 16.

FIG. 16 is an end elevational view of the folder in the folded position.

DESCRIPTION OF THE PREFERRED EMBODIMENTS

Figure 9:
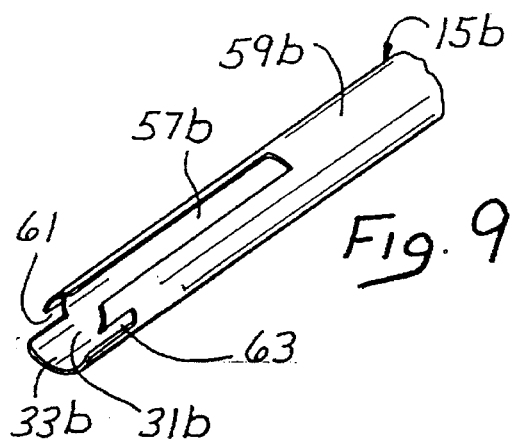
FIG. 9 is a perspective view of a third form of tubular member.

FIG. 1 shows an IOL 11 which can be inserted by forceps 13 into a tubular member 15. Both the IOL 11 and the forceps 13 may be of conventional construction. The IOL 11 comprises an optic 17 of foldable or deformable material, such as silicone based or acrylic based material and identical fixation members 19 and 21 coupled to the optic. The optic 17 can be folded from the normal configuration shown in FIG. 1 and is sufficiently resilient and has sufficient memory such that upon insertion into the eye, it recovers to its normal configuration. In the form shown in FIG. 1, the fixation members 19 and 21 each include a resilient strand of a suitable resilient material, such as polypropylene or polymethylmethacrylate, and these members are used to fix or retain the IOL 11 in the eye following implantation. The particular form of the IOL shown in FIG. 1 is purely illustrative.

The forceps 13 includes arms 23 which can be moved between an open position of FIG. 1 in which the arms are spaced apart and a closed position in which the arms are moved toward each other by levers 25. The levers 25 are normally held apart by springs 27 such that the arms 23 are normally spring biased to the open position. However, by moving the levers 25 toward each other, the arms 23 are likewise moved toward each other to a closed position. Forceps of this type can be purchased from Back-Mueller Inc. of St. Louis, Mo. Of course, forceps of other kinds and configurations may be employed.

The tubular member 15 has a central axis 29, a cylindrical bore 31 opening at opposite ends of the bore in openings 33 and 35 and an end face 37 at the opening 33 which is inclined relative to the central axis 29 to provide a platform 39. Thus, the opening 33 opens both axially and radially of the bore 31. The bore 31 may be of other cross sectional configurations such as elliptical. The end face 37 is inclined relative to the central axis at an acute angle which may be, for example, about 30 degrees. The bore 31 is sized and adapted to receive the IOL 11 in a folded condition and to hold the IOL in that folded condition. As such the bore 31 may have an internal diameter of about 0.100 inch.

Although various constructions are possible, the tubular member 15 is in the form of a tube. The tubular member 15 is attached to a central region of a plate 43, and the plate provides opposite flanges 45 which extend laterally outwardly of the tubular member and which facilitate manual manipulation of the tubular member 15. The tubular member 15 and the plate 43 may be constructed of any suitable rigid material with a metal such as stainless steel being-preferred. However, other materials, such as a suitable polymeric material, may also be employed.

To carry out the method of this invention utilizing the tubular member 15, the IOL 11 is folded in a conventional manner utilizing the forceps 13 and conventional techniques. As shown in FIG. 2, the IOL is folded approximately in half generally along a diameter of the optic 17 to provide a first fold 47. In this example, the IOL 11 as shown in FIG. 2 is in a first folded condition, and it is held in that condition by the forceps 13.

To fold the IOL into a second folded condition, the IOL is urged or pressed against the surface 49 of the platform 39 using the forceps as shown in FIGS. 2A and 2B. The surface 49 is concavely curved and helps fold the IOL 11 into a second folded condition in which the IOL has second and third folds 51 and 53 and in which the IOL is generally in the form of a W. In forming the W configuration, portions of the optic 17 fold around the arms 23, respectively, of the forceps as shown in FIG. 2A. The fold 47 opens in a direction opposite from the direction in which the folds 51 and 53 open.

Next, the IOL 11 is retained in the second folded condition in the tubular member 15. Because the platform 39 is at one end of the bore 31 and of the tubular member 15, it is a simple matter to advance the IOL in the second folded condition into the bore as shown in FIG. 3.

With the IOL 11 retained in the tubular member 15, it can easily be transferred in, or substantially in, the second folded condition to the eye 55 (shown schematically in FIG. 5) of the patient. This can be accomplished by pushing the IOL 11 through the tubular member 15 utilizing, for example, the forceps 13 as shown by way of example in FIG. 5. Alternatively, the IOL 11 can be released by the forceps 13 and a pushing implement or plunger can be used to push the IOL through the tubular member and an incision into the eye 55. Pushing of the IOL 11 through the tubular member 15 is preferred because as the IOL exits through the opening 35, it gradually unfolds thereby progressively releasing the energy stored in the folded IOL. This progressive release of energy tends to reduce the likelihood of injury that might result from too rapid a release of energy from the folded IOL 11.

FIG. 6–8 show a tubular member 15a which is identical to the tubular member 15 in all respects not shown or described herein. Portions of the tubular member 15a corresponding to portions of the tubular member 15 are designated by corresponding reference numerals followed by the letter a. A primary difference between the tubular member 15a and the tubular member 15 is that the former has an opening 57 in a peripheral wall 59 of the tubular member. The opening 57, which in this embodiment is an elongated axially extending slot, leads to the bore 31a and opens at the opening 33a. The opening 57 is sized and adapted to allow passage of the IOL 11a in the first folded condition through the opening and into the bore 31a. As such the opening 57 preferably has a minimum width of about 5 millimeters. The tubular member 15a also has a platform 39a.

In use of the tubular member 15a, the IOL 11 is held in the first folded condition by the arms 23 of the forceps as shown in FIG. 7 and is inserted through the opening 57 into the bore 31a. This urges the IOL 11 against the surface 49a which defines the bore 31a to fold the IOL into the second folded condition as shown in FIG. 8 in which the IOL is generally in the form of a W as viewed in end elevation. The arms 23 of the forceps also pass through the opening 57 in moving the IOL from the position shown in FIG. 7 to the position shown in FIG. 8. Alternatively, the platform 39a can be used as described above in connection with (FIGS. 1-5) to fold the IOL into the second folded condition. From there, the IOL 11 may be transferred through an incision into the eye 55 of the patient by the forceps 23 as described above in connection with FIG. 5 or by a separate plunger.

Figure 10:
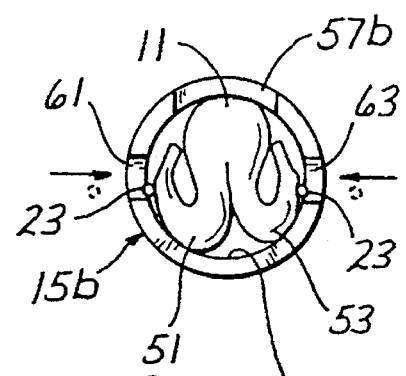
FIG. 10 is an end elevational view illustrating the use of forceps to remove the IOL in the second folded condition from the tubular member of FIG. 9.
Figure 11:
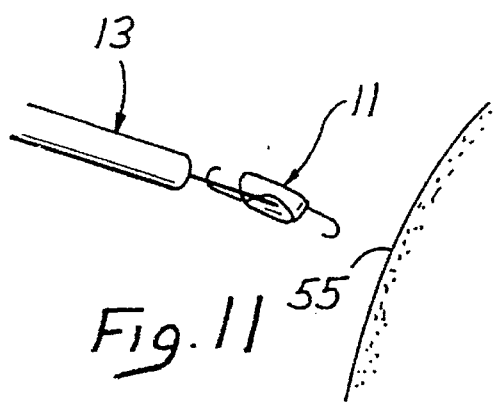
FIG. 11 shows the IOL of FIG. 10 in the second folded condition removed from the tubular member of FIG. 9 and about to be inserted with forceps through an incision into the eye of a patient.

FIGS. 9 and 10 show another form of tubular member 15b and FIGS. 10 and 11 show a preferred technique for transmitting the folded IOL from the tubular member 15b to the eye of a patient. The tubular member 15b is identical to the tubular member 15 in all respects not shown or described, and portions of the tubular member 15b corresponding to portions of the tubular member 15 are designated by corresponding reference numerals followed by the letter b.

Briefly stated, the tubular member 15b may be identical to the tubular member 15a except that the former has no platform and has first and second generally opposed and axially extending slots 61 and 63 opening at the opening 33b. The slots 61 and 63 are sized to receive the arms 23, respectively, of the forceps as shown in FIG. 10. The tubular member 15b also has an opening 57b in the peripheral wall 59b leading to the bore 31b. The opening 57b is, like the opening 57a, in the form of a slot, and it is preferably centered between the slots 61 and 63.

The IOL 11 may be folded into the first folded condition using forceps and also held in the first folded condition as shown in FIG. 2 by forceps. The IOL 11 is inserted through the slot 57b into the tubular member 15b as described above in connection with FIGS. 7 and 8 to fold the IOL 11 into the second folded condition utilizing the surface 49b within the tubular member. Next, the IOL 11 can be withdrawn in the second folded condition from the tubular member 15b utilizing an insertion tool, such as the forceps 13, and inserted into the eye 55 of the patient using the forceps as shown in FIG. 11. To withdraw the IOL from the tubular member 15, the arms 23 oft he forceps are passed through slots 61 and 63 as shown in FIG. 10 such that the forceps can grip the IOL and retain it in, or substantially in, the second folded condition. The forceps are used to withdraw the IOL 11 by pulling it in substantially the second folded condition out through the open end 33b. The forceps are then used to insert the IOL through an incision into the eye 55 (FIG. 11) in accordance with known surgical procedures.

FIG. 12 shows a folder 65 which can be used to fold the foldable IOL 11 for insertion into the eye of a patient. In this embodiment, the folder 65 includes first and second jaws 67 having concave surfaces 69 of semicylindrical configurations and being sized and configured to receive the IOL 11. A hinge 71 joins the first and second jaws 67 for pivotal movement about an axially extending pivot axis between a loading position shown in FIG. 13 in which the concave surfaces 69 are sufficiently out of confronting relationship so that the first and second jaws can receive the IOL 11 and a folded position shown in FIG. 16 in which the concave surfaces are in generally confronting relationship. Preferably, the folder 65 is constructed from a suitable polymeric material, such as polypropylene, which will enable the hinge 71 to be a living hinge formed of the material of the folder. The jaws 67 are adapted to fold the IOL 11 in moving from the loading position of FIG. 13 to the folded position of FIG. 16 as described more fully below.

The jaws 67 have opposite ends and the jaws define generally opposed slots 73 and 75 which open at one of the ends for receiving arms 77 of forceps 79. FIG. 12 shows by way of example a second type of conventional forceps 79 that can be used to carry out the method of this invention. Although various constructions are possible, in this embodiment, the slot 73 is formed by an absence of material in an axially extending region of the folder at the base of the jaws 67 and the slot 75 is formed by spacing apart free edges 81 of the Jaws 67. The folder 65 also includes first and second tabs 83 extending longitudinally along the free edges 81, respectively, and coupled to the jaws 67 for use in moving the jaws between the two positions of the Jaws. The tabs 83 are spaced apart in the folded condition to provide access to the slot 75.

In use of the folder 65, the IOL 11 is placed on the jaws 67 with the Jaws in the open or loading position (FIG. 13) and the jaws are pivoted to the folded position of FIG. 16. This causes the jaws to fold the IOL 11 in generally the manner shown in FIGS. 14 and 15. It may be desirable to utilize one or more of the arm 77 of the forceps to assist with the folding.

The folder also constitutes a tubular member which can be used to retain the IOL in the folded condition pending removal of the folded IOL for insertion into the eye of the patient. In the folded condition shown in FIG. 16, opposite edge portions 85 and 87 of the optic 17 are overlapped and the main body portion of the optic is in the form of a roll conforming generally to the shape of the concave surfaces 69 as viewed in end elevation (FIG. 16).

To remove the IOL 11 from the folder 65, the arms 77 of the forceps 79 are passed through the slots 73 and 75, respectively, and caused to grip the folded IOL 11. The IOL 11 is then pulled in substantially this folded condition from the folder 65 with the forceps 79. The folded IOL 11 can then be inserted through an incision into the eye of the patient using the forceps 79, and this can be accomplished in a generally known manner.

Figure 17:
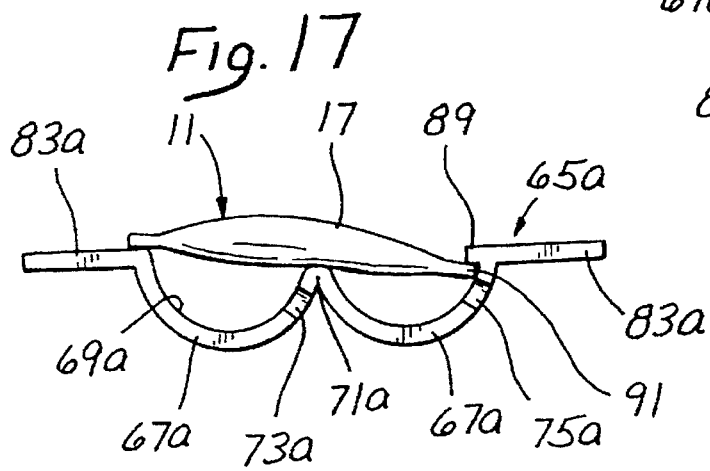
FIG. 17 shows a second embodiment of folder in the loading position together with an IOL.
Figure 18:
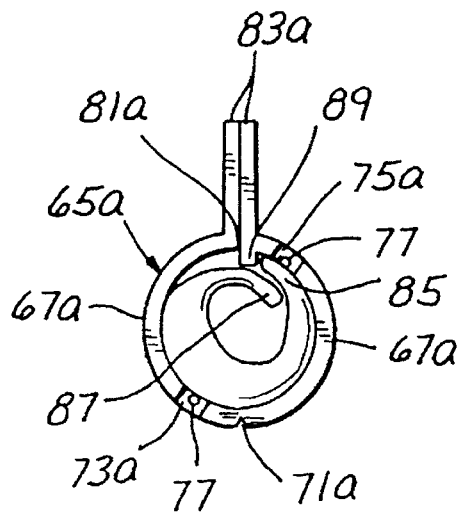
FIG. 18 is an end elevational view of the folder of FIG. 17 in the folded position.

FIGS. 17 and 18 show a folder 65a which is identical to the folder 65 in all respects not shown or described herein. Portions of the folder 65a corresponding to portions of the folder 65 are designated by corresponding reference numerals followed by the letter a.

One difference between the folders 65 and 65a is that the latter has generally opposed elongated slots 73a and 75a which are circumferentially offset from the free edges 81a. Also, both of the slots 73a and 75a are formed in the jaws 67a, respectively.

Another difference between the folder 65a and 65 is that the folder 65a has a retainer in the form of a flange 89 on one of the jaws 67 at the free edge 81a of that jaw. One edge 91 of the optic 17 may be placed under the flange 89 in the loading position of FIG. 17. The flange 89 retains the edge 91 as the folder 65a is pivoted about the hinge 71a from the loading position of FIG. 17 to the folded position of FIG. 18. The flange 89 also tends to direct the edge portion 87 of the optic 17 beneath the edge portion 85 as shown in FIG. 18. Thus, the folder 65a functions in essentially the same manner as the folder 65. Also, arms 77 of the forceps 79 can be used to remove the IOL in substantially the folded condition from the folder 65a as shown in FIG. 18 and inserted through an incision into the eye of a patient using the forceps as shown in FIG. 11.

Although exemplary embodiments of the invention have been shown and described, many changes, modifications, and substitutions may be made by one having ordinary skill in the art without necessarily departing from the spirit and scope of the invention.

What is claimed is:

1. A folder for folding an intraocular lens which has a resiliently deformable optic, said folder comprising:

first and second jaws, said jaws having concave surfaces and being sized and configured to receive an intraocular lens;

a hinge, said hinge joining the first and second jaws for pivotal movement between a loading position in which the concave surfaces are sufficiently out of confronting relationship so that the first and second jaws can receive the intraocular lens and a folded position in which the concave surfaces are in generally confronting relationship, said jaws being adapted to fold the intraocular lens in moving from the loading position to the folded position; and said jaws in the folded position having opposing first and second ends which are located on opposite ends of said hinge, respectively, and both of said jaws together defining each of two generally opposed slots which open at one of said opposing first and second ends for receiving arms of a forceps, at least one of said generally opposed slots being closed at the other of said opposing first and second ends.

2. A folder as defined in claim 1 including a flange on one of the jaws for retaining an edge of the intraocular lens.

3. A folder as defined in claim 1 wherein each of said first and second jaws has a free edge, said folder includes first and second tabs adjacent the free edges on the first and second jaws, respectively, for use in moving the jaws from the loading position to the folded position, said free edges being spaced apart in said folded position to define one of said slots, and said tabs being spaced apart in said folded position to provide access to said one slot.

4. A folder for folding an intraocular lens which has a resiliently deformable optic, said folder comprising:

first and second jaws, said jaws having concave surfaces and being sized and configured to receive an intraocular lens;

a hinge, said hinge joining the first and second jaws for pivotal movement between a loading position in which the concave surfaces are sufficiently out of confronting relationship so that the first and second jaws can receive the intraocular lens and a folded position in which the concave surfaces are in generally confronting relationship, said jaws being adapted to fold the intraocular lens in moving from the loading position to the folded position; and said jaws in the folded position having opposing first and second ends which are located at opposite ends of said hinge, respectively, each of said first and second jaws defining a slot which opens at said first end for receiving arms of a forceps provided that at least one of said slots is closed at said second end.

5. A folder as defined in claim 4 wherein said slots are oriented to be generally opposing with said jaws in the folded position.

6. A folder as defined in claim 4 including a flange on one of the jaws for retaining an edge of the intraocular lens.

* * * * *